US009023408B2

(12) United States Patent
Meyer

(10) Patent No.: US 9,023,408 B2
(45) Date of Patent: May 5, 2015

(54) COMPOSITION AND METHOD FOR CONTROL OF DIABETES

(75) Inventor: James H. Meyer, Santa Monica, CA (US)

(73) Assignee: Meyer Nutriceuticals LLC, Santa Monica, CA (US)

( * ) Notice: Subject to any disclaimer, the term of this patent is extended or adjusted under 35 U.S.C. 154(b) by 97 days.

(21) Appl. No.: 13/254,833

(22) PCT Filed: Mar. 3, 2010

(86) PCT No.: PCT/US2010/026097
§ 371 (c)(1),
(2), (4) Date: Oct. 3, 2011

(87) PCT Pub. No.: WO2010/102041
PCT Pub. Date: Sep. 10, 2010

(65) Prior Publication Data
US 2012/0040048 A1    Feb. 16, 2012

Related U.S. Application Data

(60) Provisional application No. 61/157,348, filed on Mar. 4, 2009.

(51) Int. Cl.
| | | |
|---|---|---|
| A23K 1/18 | (2006.01) | |
| A23L 1/00 | (2006.01) | |
| A61K 9/50 | (2006.01) | |
| A23L 1/30 | (2006.01) | |

(52) U.S. Cl.
CPC ............. *A61K 9/5026* (2013.01); *A23L 1/0017* (2013.01); *A23L 1/0052* (2013.01); *A23L 1/0064* (2013.01); *A23L 1/3008* (2013.01); *A23V 2002/00* (2013.01)

(58) Field of Classification Search
CPC ... A23L 1/0017; A23L 1/0052; A23L 1/0064; A23L 1/3008; A61K 9/5026; A23V 2002/00; A23V 2200/328; A23V 2200/22; A23V 2250/186
USPC ..................................................... 426/2, 89
See application file for complete search history.

(56) References Cited

U.S. PATENT DOCUMENTS

| 5,753,253 | A | 5/1998 | Meyer | |
|---|---|---|---|---|
| 6,267,988 | B1 * | 7/2001 | Meyer | ........................... 424/489 |
| 2003/0203004 | A1 * | 10/2003 | Kelm et al. | ................... 424/439 |
| 2006/0246085 | A1 | 11/2006 | Lin | |
| 2009/0311367 | A1 * | 12/2009 | Perry | ............................... 426/2 |

FOREIGN PATENT DOCUMENTS

| EP | 1967183 A1 | 9/2008 |
|---|---|---|
| WO | WO 87/03198 * | 6/1987 |
| WO | WO 2004/022074 A1 | 3/2004 |
| WO | WO 2004/105520 A1 | 12/2004 |
| WO | WO 2005/089786 A2 | 9/2005 |
| WO | WO 2006136161 A2 * | 12/2006 |

OTHER PUBLICATIONS

Malijaars et al (2010). "An ileal brake-through?" Am J Clin Nutri., 92:467-468.*
Cuche et al (2000). "Ileal short-chain fatty acids inhibit gastric motility by humoral pathway." Am J Physiol Gastroinitest Liver Physio., 279: G925-G930.*
Ohtani et al (2001). "Mediator for Fat-induced Ileal brake are different between stomach and Proximal Small Intestine in Conscious Dogs." J Gastrointest Surg., 5: 377-382.*
Moran-Ramos et al (2012). "Diet: Friend and Foe of Enteroendocrine Cells: How It interacts with Enteroendocrine Cells." Adv. Nutr., 3: 8-20.*
Torgerson et al. (Jan. 1, 2004). "Xenical in the Prevention of Diabetes in Obese subjects (XENDOS) study." Diabetes Care, 17(1): 155-161.*
Feltrin et al (2007). "Effects of Lauric acid on upper gut motility, plasma cholecystokinin and peptide YY, and energy intake are load, but not concentration, dependent on humans." J Physiol, 581.2: 767-777.*
Debunne, Ann et al., "Compaction of enteric-coated pellets: influence of formulation and process . . . ", *European Journal of Pharmaceutical Sciences*, vol. 22, No. 4, Jul. 1, 2004, pp. 305-314. XP002449822.
Maljaars, P W J et al., "Effect of ileal fat perfusion on satiety and hormone release in healthy volunteers", *International Journarl of Obesity*, vol. 32, No. 11, Nov. 2008, pp. 1633-1639. XP002613622.
Meier J J et al., "Glucagon-like peptidse 1 as a regulator of food intake and body weight: therapeutic perspectives," *European Journal of Pharmacology*, vol. 440, No. 2/03, Apr. 12, 2002, pp. 269-279. XP001113094.
J. Ma et al., "Effects of enterically coated, nutrient-containing pellets on glycaemia and incretin hormone release in type 2 diabetes", *Journal of Gatroenterology and Hepatology*, vol. 25, No. Supp. 3, Jan. 1, 2010, pp. A114-A115. XP002613623.

* cited by examiner

*Primary Examiner* — Anoop Singh
*Assistant Examiner* — Doan Phan
(74) *Attorney, Agent, or Firm* — Venable LLP; Stefan J. Kirchanski

(57) ABSTRACT

Correctly formulated enterically coated nutrient pellets are able to significantly to lower the blood sugar level of type two diabetics when administered with a normal meal. The inventive composition is effective at dosage levels of 10 g or less. Effective doses of the composition contribute 42 kcal or fewer to the patient's diet. A preferred form of the composition contains lauric acid coated for release in the distal bowel. When taken with an ordinary meal, the effective dosage does not induce the ileal brake and is more than 50 times (often more than 100 times) as effective on per kilocalorie basis as an ordinary meal at eliciting increases in PYY and GLP-1. Thus, ordinary nutrients—as opposed to drugs—can be used to reduce blood sugar levels when administered at dosage levels that are not significant promoters of weight gain.

11 Claims, 9 Drawing Sheets

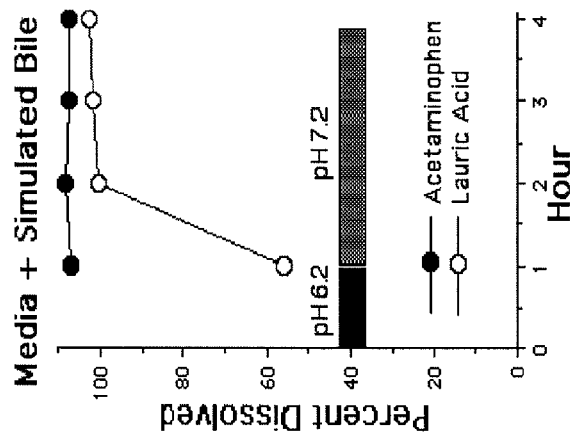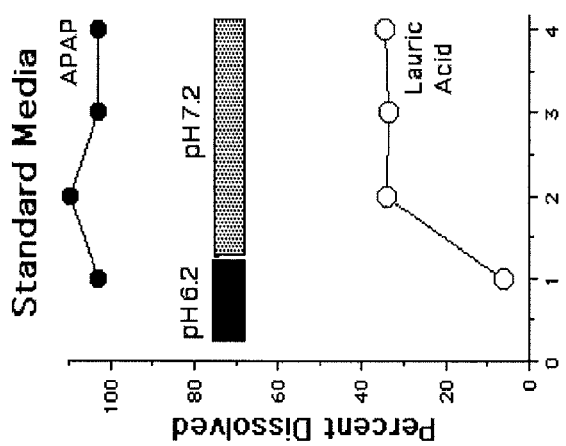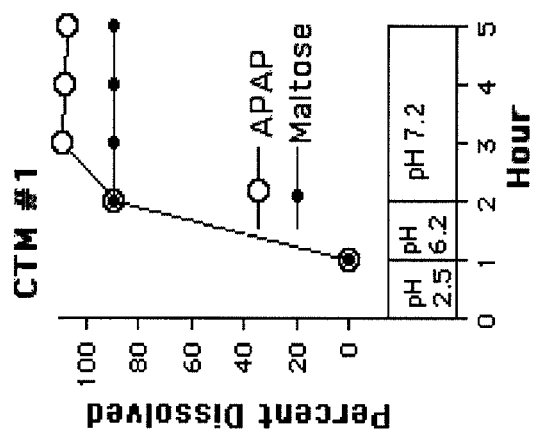

COMPOSITION AND METHOD FOR CONTROL OF DIABETES

CROSS-REFERENCE TO PRIOR APPLICATIONS

The present application is a non-provisional version of U.S. Provisional Patent Application 61/157,348 (filed 4 Mar. 2009) and claims benefit and priority from that application.

U.S. GOVERNMENT SUPPORT

N/A

BACKGROUND OF THE INVENTION

Area of the Art

The present invention concerns the use of ordinary nutrients to control diabetes and a composition formulated for such use.

DESCRIPTION OF THE BACKGROUND ART

Obesity may lead to ill health in several ways, but among the more serious of its associated morbidities is type 2 diabetes. Although one does not have to be obese to develop type 2 diabetes, and not all obese individuals develop diabetes, obesity is, nevertheless, a major risk factor for type 2 diabetes. For example, type 2 diabetes was rare among children in previous decades with type 1 diabetes representing almost all diabetes cases in the pediatric age group, but as the prevalence of childhood obesity has increased, so also has juvenile type 2 diabetes. At the present time, type 2 diabetes accounts for nearly one third of all cases of diabetes among children ages 10-19. Type 2 diabetes in children is the predominant form of diabetes among African Americans, American Indians, and Americans of Hispanic or Asian/Pacific origins, groups of Americans in which obesity is also most prevalent. Because of the recent worldwide epidemic of obesity, an epidemic of type 2 diabetes looms as the obese age. Therefore, there is a need for a simple, safe, cheap, and effective treatment for type 2 diabetes.

Long standing, abnormally high concentrations of glucose in the blood that arise from either type 1 or type 2 diabetes lead to serious complications, such as stroke or heart attacks, blindness, kidney failure and degeneration of nerves. In obesity, increased body fat leads to insulin resistance in direct proportion to the magnitude of excess fat because fat cells secrete substances that diminish the effectiveness of insulin on lowering blood sugar. To counteract this insulin resistance, the insulin secreting cells of the pancreas (beta cells) must secrete increased quantities of insulin. As time goes on, the beta cells eventually become exhausted and die in individuals who are susceptible to type 2 diabetes; as a result, secretion of insulin diminishes, and blood sugar (glucose) concentrations rise to abnormal levels, heralding the clinical onset of this disease. At first, blood sugars are elevated only over a few hours after eating carbohydrates; but as beta cell secretion further deteriorates, the post prandial increase in blood sugar no longer falls back to normal levels. Risk of complications of diabetes increases with the product of the duration of elevated blood glucose and the level of the elevation. Reducing blood glucose concentrations significantly over prolonged periods diminishes the risks of complications. For example, lowering the percentage of hemoglobin A1C (abnormal glycosylated hemoglobin which is a measure of the level and duration of elevated glucose concentrations in the blood) from 8 to 7%, lowers the risk of eye, kidney, or nerve diseases by 40%.

Several short-term studies suggest that weight loss induced by dietary restriction and exercise significantly reduces the subsequent incidence of clinical diabetes in obese subjects who are already exhibiting some elevation of blood sugar (although not enough to be called overtly diabetic) and/or insulin resistance ("pre-diabetes"). However, the ability to sustain weight loss by life style modifications alone has proven difficult. For example, in one of these studies a 7 kg loss in of body weight achieved in the first year of the study diminished to a 4 kg (4.2%) reduction by 30 months of follow up and beyond. Nevertheless, this small amount of weight loss, in combination with an exercise program, lowered blood glucoses in a substantial proportion of subjects. On the basis of studies like these it has often been stated that as little as a 5% reduction in body weight (about the maximum weight reduction that can be sustained by diet or currently available drugs) will bring significant benefit to obese, overtly diabetic subjects. Since both insulin resistance and incidence of type 2 diabetes in susceptible individuals increase directly with excess fat mass, the amount of weight reduction needed to reverse diabetes or prevent progression of pre-diabetes to clinical diabetes will, of course, depend on how obese a given individual is at the start of treatment.

In addition to life style (diet and exercise) changes, surgery has become a possible option for control of obesity. For example, a randomized controlled trial in substantially obese subjects (Body Mass Index (BMI)=37 kg/m$^2$) comparing life style modification with the bariatric surgery, laparoscopic adjustable banded gastroplasty (LABG) demonstrated reversal of early type 2 diabetes in 21 of 25 individuals who, after LABG, lost more than 10% of body weight, but remission in only 1 of 5 operated subjects who lost 10% or less [1.]. The control subjects lost only 1.7% (on average) over the two years of the study and only 2 of the 29 control subjects who lost less than 10% of body weight showed a reversal of diabetes (the 30th control subject who lost 15% of body weight experienced a reversal of diabetes). This study illustrates two realities: (a) despite rigorous medical supervision, it was difficult for the control subjects to achieve substantial weight loss; yet (b) remission of type 2 diabetes in substantially obese individuals requires more weight reduction than can be obtained by current medical treatment in the vast majority of obese, diabetic individuals.

The present inventor has long been interested in problems of obesity and has been involved in the development of enteric coated dosage forms targeted for release of core nutrients in the ileum and/or colon as a means for controlling obesity. To date, the inventor has created and tested three prototypes that he calls "clinical testing materials" (CTMs). The inventor has obtained four United States Patents covering these inventions.

In 1987, Pories [2.] reported that morbidly obese, diabetic patients experienced a marked amelioration of their type 2 diabetes within days after undergoing Roux-en-Y gastric bypass (RYGBP), an operation that surgically diverts digesting nutrients to the ileum. Blood sugar (glucose) levels were lowered in these individuals before substantial weight was lost. Since then many others have confirmed this phenomenon after RYGBP, and others have reported that biliopancreatic diversion (BPD) (a bariatric surgery that diverts digesting nutrients to the distal ileum and colon) similarly rapidly ameliorates diabetes. Additionally, several studies in diabetic rats that have undergone a variety of surgical gut rearrangements have confirmed that exposing even short segments of the ileum to digesta lowers blood sugar. The ileum and, even more so, the colon contain high populations of L cells that are rare in the more proximal intestine. When contacted by digestive products from each of the three macronutrients (lipids, proteins and carbohydrates), these cells secrete the peptides, glucagon-like intestinal peptide-1 (GLP-1), glucagon-like peptide-2 (GLP-2), and peptide YY (PYY). GLP-1 is known to be capable of lowering blood sugar through a variety of mechanisms. There are now many reports of high post prandial elevations of GLP-1 after RYGBP or BPD, and the growing consensus is that GLP-1 mediates the amelioration of type 2 diabetes that follows these bariatric surgeries.

That release of endogenous GLP-1 may account for a dramatic lowering of blood sugar in diabetic patients following these diverting surgeries is an idea now also well supported by a variety of clinical observations with pharmaceutical agents that enhance the actions of GLP-1. Bioactive GLP-1 is secreted from L cells as a 7-36 peptide, but an enzyme dipeptylpeptidase-4 (DPP-4) located along capillary walls rapidly degrades the active GLP-1$_{7-36}$ peptide to inactive GLP-1$_{9-36}$ by splitting two amino acids from the N-terminal, so that the half life of active GLP-1$_{7-36}$ is less than 90 seconds. Sitagliptin® and Vildagliptin® each potently inhibit DPP-4 and in doing so raise blood concentrations of bioactive GLP-1$_{7-36}$ by 20% under fasting conditions and by 100% post prandially. The result is a substantial lowering of post prandial blood glucose in subjects who have type 2 diabetes. The effects of higher levels of bioactive endogenous GLP-1 are mediated via the autonomic nervous system mainly to suppress secretion of glucagon from the alpha cells of the pancreas and to increase glucose uptakes by liver and muscle. Synthetic, parenterally administered, GLP-1 analogs (Baeta,® Liraglutide®) have much longer bioactive half-lives, so that much higher, pharmaceutical levels of GLP-1-like bioactivity can be sustained. In addition to the above actions, the exogenous, GLP-1 analogs, when given at high doses, lower glucose by (a) slowing gastric emptying of ingested carbohydrate and (b) by directly stimulating the pancreatic beta cells to release insulin. The major advantages of all of these GLP-1 promoting drugs are twofold: (1) they lower only abnormally elevated concentrations of blood glucose and will not evoke a hypoglycemic reaction and (2) they do not promote weight gain, like other anti-diabetic medicines (e.g., insulin, sulfonylureas).

However, knowing that generally bathing the distal intestine with nutrients can have a beneficial effect by releasing GLP-1 (or perhaps other agents) provides no specifics on how to overcome several potential problems. (a) Which nutrient(s) are most effective? (b) How can the optimal nutrients be brought to the ileum without surgical treatment? (Normally, nutrients entering the small intestine are so rapidly digested and absorbed that none or only a small fraction reaches the ileum.) (c) Asking individuals with type 2 diabetes (many of whom are already obese) to consume additional nutrients as a therapy raises the very real potential of caloric excess and concomitant deleterious weight gain. Therefore, some method has to be employed to make very small quantities (that is, minimal extra calories) highly effective. (d) To effectively lower post-prandial blood glucose, nutrients must reach the ileum very soon after ingestion of a meal and must continuously bathe the ileum for 3-4 hours following the meal; that is, for the post-cibal period of gastric emptying of carbohydrates. How can such delivery be achieved? (e) Wouldn't nutrients released into the ileum trigger the ileal brake to slow gastric emptying and small intestinal transit? Nutrient digestive products from fat, carbohydrate and protein are known to produce inhibition of transit. This inhibition is potentially deleterious in two ways: (i) it may aggravate diabetic gastroparesis and more importantly, (ii) nutrients initially reaching the ileum may significantly slow gastric emptying and jejunal transit of remaining nutrient targeted to ileum, thereby limiting their rate of ileal delivery and the effectiveness of the overall treatment.

SUMMARY OF THE INVENTION

As discussed above, digestive products of macro nutrients release GLP-1 and other effector molecules in the distal intestine. While digestive products from all three macronutrients can potentially release GLP-1 or other effector molecules on contact with L cells, fatty acids (digestive products of lipids) have two potential advantages over oligosaccharides and monomeric sugars (digestive products of carbohydrates) or oligopeptides and free amino acids (digestive products of proteins). Oligosaccharides are rapidly converted to short chain fatty acids, and amino acids are rapidly deaminated by colonic bacteria into short chain organic acids; whereas fatty acids undergo little catabolism in colon. Short chain fatty acids from degradation of carbohydrate in the human colon do not stimulate release of GLP-1 [3.]. This suggests that any spillover from the ileum into the colon (intentional or not) of dosage forms that deliver a fatty acid may still allow the fatty acid to stimulate L cells in the colon to release GLP-1. Second, fatty acids that release peptides, like GLP-1 and PYY, (that is, those with chain lengths of 12 carbons or longer [4.]) are, depending on chain length, much less water soluble than many oligo- or mono-saccharides or many amino acids and are also less rapidly absorbed from the intestinal lumen.

These distinguishing features mean that after release from an enteric coating, fatty acids will persist in the lumen for a longer time, with a greater length of spread, independent of coating, while they are being dissolved and then absorbed. By contrast, small amounts of highly soluble, rapidly absorbed sugars, like maltose, can achieve a luminal spread only by virtue of slow release from a coating. Nevertheless, its is conceivable that some kind of coating alone could be found to be suitable for control of glucose in diabetics by enterically coated maltose or amino acid. Because of these theoretical considerations, work was focused on a fatty acid preparation including lauric acid which is the most water soluble of soluble of the peptide stimulating fatty acids.

This disclosure describes the use of enterically coated pellets of fatty acid such as lauric acid, ingested with food to stimulate the ileum for the purpose of lowering blood sugar concentrations in subjects with type 2 diabetes. The preferred, but not exclusive, embodiment is 0.5-3 mm pellets of lauric acid coated with Eudragit L100. The advantages of this preferred embodiment are several:

A). Of the peptide-releasing fatty acids, lauric acid is sufficiently soluble to dissolve from the dosage form in both ileum and even in colon, where it releases GLP-1 and PYY (and perhaps other) effector peptides that act to suppress blood glucose.

B). This solubility, together with a slow release from the dosage form, that lasted up to 330-360 minutes after ingestion, allowed pellets ingested with breakfast to continue to act in colon in concert with pellets, newly ingested with lunch, to produce an enhanced lowering of blood glucose, as breakfast-time pellets still releasing in colon acted synergistically with lunch-time pellets releasing in ileum to produce a release of GLP-1 (and/or possibly other peptides) that was greater than GLP-1 released from pellets confined to ileum in the 240 minutes after the morning dose. This synergism favors a treatment where a pellet dose is provided with each meal.

C). Unexpectedly, the released lauric acid did not inhibit gastrointestinal transits; i.e., showed no ileal braking. The lack of ileal braking allowed very rapid, post cibal transit to the ileum, so that pellets could quickly spread along the ileum. The result was a significant lowering (vs. placebo control) of post prandial glucose as early as 45 minutes after the meal. In view of this pattern of rapid transit to ileum, a faster dissolving coating (resulting from being thinner and/or of a different composition) will reduce post prandial glucose even earlier than 45 minutes after a meal. Because gastric emptying is often delayed in type 2 diabetics and such delays may result in exacerbation of symptoms, the fact that coated lauric acid (CTM #3) does not inhibit gastric emptying is a further advantage.

D). Although the inventors previous patents suggested there could be a relatively large effect from small amounts of nutrients as the result of spreading release of a specific nutrient from enterically coated pellets along a considerable length of small intestine, results described herein are the first actual demonstration of such magnification and the first indication of an effect on blood glucose. On a per calorie basis, lauric acid was more than 50 times—actually 77-150 times—as potent as dietary nutrients in releasing GLP-1 and PYY. It is likely that other effector molecules were also released. Thus, CTM #3 effectively overcame low post cibal GLP-1 levels that characterize type 2 diabetes. The small number of additional calories per medical dose of CTM #3 adequate to lower blood glucose effectively in, often already obese, diabetic subjects indicates that weight gains from use of such a nutrient-based medication will not increase obesity.

It will be appreciated that while CTM #3 alone can result in significant blood glucose reduction in type 2 diabetics, this effect can be modulated by including other nutrients in the CTM. In particular, inclusion (blending) of other fatty acid species with the lauric acid can alter the results. It will be further appreciated that the present invention includes the use of one or more fatty acids. It is also possible to include complex fats and waxes in the CTM so that enzymatic breakdown of such macromolecules continually releases a supply of effective fatty acids. In addition, dissolution and spread can be affected by including proteins/peptides and/or polysaccharides/sugars. Such blending of nutrients does not depart from the present invention which contemplates the delivery of specific nutrients to the distal intestine in such a manner as to elicit effector molecules which lower blood sugars in diabetics with a caloric efficiency at least 50 times as great as that of normally ingested nutrients.

DESCRIPTION OF THE FIGURES

FIG. 1 shows graphs of U.S.P. in vitro dissolution under different conditions; FIG. 1a shows CTM #1 at different pHs; FIG. 1b shows CTM #3 at different pHs; and FIG. 1c shows CTM #3 at different pHs in simulated bile.

FIG. 3 shows the ileal brake induced by ingestion of CTM#1.

FIG. 8b illustrates another way of interpreting the data of FIG. 7a.

DETAILED DESCRIPTION OF THE INVENTION

Figure 2B:
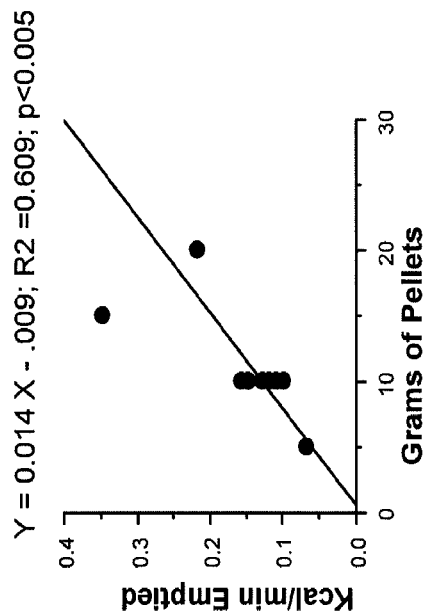
FIG. 2a shows gastric emptying of CTM #3 and FIG. 2b shows the amount of nutrient bathing the distal gut following the emptying of CTM #3

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide a composition containing enterically coated nutrients which can be used to lower the blood sugar of type 2 diabetics without appreciably increasing the ingestion of calories.

A major goal of the present invention is to use nutrients introduced into the distal bowel to modulate blood sugar. This is difficult to achieve particularly without significantly increasing a patient's caloric intake. The difficulty of getting sufficient nutrient into the ileum to modulate blood sugar but not so much as to create an obesity promoting, caloric excess can perhaps be illustrated with Acarbose®, a drug sometimes prescribed to diabetics. In the normal intestine, digestion and absorption of food is so efficient, that few digestive products reach the ileum; and almost none reach the colon. Only after very large meals (when nutrients enter small intestine at very high rates) or after meals especially high in fat or protein (which take longer to completely digest than do carbohydrates) do digestive products reach mid ileum or beyond. Acarbose® is administered orally with a mixed meal or with a pre-meal drink of 50-100 g (200-400 kcal) of sucrose. The drug competitively inhibits å-glucosidases which are located at the mucosal brush border surfaces. These oligosaccharidases are required to convert oligosaccharides into monomeric sugars that can be readily absorbed, whether the oligosaccharides are in the diet (as with sucrose) or are the end products of luminal digestion of starches. When Acarbose was given to normal subjects with a pre-meal drink of 50 or 100 grams of sucrose or with a high (61 g) carbohydrate meal, digestion of carbohydrate was slowed and much undigested carbohydrate reached the ileum, where glucose continued to be released, to stimulate secretion of both GLP-1 and PYY and to slow gastric emptying (the "ileal brake" effect). [5.] However, its effectiveness in slowing gastric emptying or raising post prandial GLP-1 has been much less effective in type 2 diabetics after meals with lower amounts of carbohydrate [6.] This lower efficacy may stem from the well described slower gastrointestinal transit rates in diabetics and/or from an equally well described lower release of GLP-1 by food in patients with diabetes [7.] [8.] Alternatively, the GLP-1 releasing and glucose lowering effects of Acarbose may depend heavily on the load of carbohydrate ingested, with appreciable release of glucose in the ileum only after very high carbohydrate loads.

A further illustration of attempts to use specific nutrients to stimulate secretion of GLP-1 and of insulin is the use of whey protein. In a recent study, 55 grams of whey protein were administered in an attempt to elicit a high release of endogenous GLP-1 [9.]. The whey was given as a pre-meal 30 minutes before a high carbohydrate meal or with the carbohydrate meal, versus a control of the carbohydrate meal without the whey protein. The high load of whey, whether given as a pre-meal or taken with the high carbohydrate meal, raised post prandial GLP-1 substantially over the response following the carbohydrate alone, with the increase arising earlier after the whey pre-meal than after the whey with the meal. The whey protein also raised serum insulin levels and lowered blood glucose. However, this effect on insulin stems mainly from the post-absorptive effects of leucine, isoleucine and valine on the pancreatic beta cells rather than from the elevations of GLP-1 induced by the whey [10.]. The effects of whey on GLP-1 were the result of a large, 220 kcal, protein load reaching the ileum and still not completely digested and absorbed [11.].

In both of these examples, considerable extra calories had to be consumed to achieve the desired effects—a high carbohydrate load to allow Acarbose to work and a high protein load to achieve ileal contact with whey. As will be developed below, enterically coated pellets of lauric acid in the present invention permit a prompt, substantial, and sustained elevation of GLP-1 and suppression of post prandial blood sugar in type 2 diabetics after increased caloric loads of only 21-42 kcal when pellets are taken in effective 5 g or 10 g doses. Further, preliminary data suggest that with further refinements in formulation and coating, subsequent versions of this CTM can be anticipated to achieve similar results with 2.5 g or 5 g doses. That is, only 10.5 or 21 kcal per dose, respectively or even less may be required. Because obesity is common in type 2 diabetics, using enterically coated pellets to achieve a large release of GLP-1 from only a small additional caloric load is highly desirable.

The present inventor holds four U.S. patents, one concerned with how to make pellets to produce different, desired rates of gastric emptying from the post cibal stomach (U.S. Pat. No. 4,976,949) and three on a Method and Composition for Inducing Satiety (U.S. Pat. Nos. 5,322,697, 5,753,253 and 6,267,988) which patents disclose how a small number nutrient calories can evoke large responses from a length of bowel. Each of these four patents is hereby incorporated herein by reference to the extent permitted by applicable law and rules. When taken with food to induce thereby a fed motility pattern, 1-3 mm pellets will empty from the stomach slowly in a gradual fashion over three to four hours (as demonstrated in FIGS. 1 and 2); whereas pellets will empty from the stomach in a small burst or bolus if ingested under fasting conditions. The gradual emptying of pellets from the food-filled stomach over time serves to spread pellets along the full intestinal length for many hours following ingestion. The mucosa along the full small intestinal length consists of an array of nutrient sensing organs distributed linearly along the length of the bowel. Scattered among a larger population of nutrient absorbing cells on the mucosal surface of each finger-like villous projection is a variety of specialized cells that synthesize, store, and release peptides or serotonin. Vagal afferent nerves, arterioles, venules, and lymphatic channels lie beneath the mucosal surface of each villus. Bioactive peptides (and serotonin) are released from their respective stores when the luminal surfaces of these specialized cells are contacted by specific, nutrient digestive products.

Once so released, these chemical transmitters diffuse into the sub mucosal space, where they may contact and excite the vagal nerve branches in the core of the villus, a paracrine action. Alternatively, these transmitters may diffuse into the sub mucosal venules that coalesce eventually into the portal vein or diffuse into sub mucosal lymphatic channels that coalesce into the thoracic duct, draining from there into the blood stream. Once in the blood stream, they can excite receptors remote from the intestine, an endocrine action. Under paracrine action, the intensity of the message ultimately born by the vagal afferent trunks to the brain intensifies in proportion to the number of stimulated, individual vagal branches among the nutrient-contacted villi. Under an endocrine action, the message is intensified when peptides draining into each sub mucosal, villous venule coalesce in the portal vein. In effect, each villus, in an array of thousands of villi along an intestinal length, is a repeating sensory unit that can be excited when contacted by specific nutrient digestive products in the overlying luminal fluid. The inventor has demonstrated in several different chronic animal models that the intensity of nutrient-driven stimulation of exocrine pancreatic secretions, of inhibition of gastric emptying, or of stimulation of satiety varies with the length of intestine (therefore, the number of villi) contacted.

The length of small intestine (number of villi) contacted by ingested nutrient digestive products depends on the rate (grams/minute) at which nutrient enters the small intestine. The faster undigested nutrient enters the small intestine, the longer it takes pancreatic enzymes entering the gut at limited (maximal) rates to digest nutrients; and since nutrients entering the proximal post cibal gut continue to be transported along intestine, the longer it takes to complete digestion, the greater the length of intestine exposed to digestive products. Moreover, each centimeter of gut has a finite, maximal rate of absorption. Therefore, even a completely digested nutrient, like glucose, entering intestine will require a greater and greater length of gut to be completely absorbed as the nutrient enters the gut at faster and faster rates. When digesta are diverted from the duodenum of experimental animals via a duodenal fistula, so that gut sensors are not contacted, the speed at which nutrient enters and is diverted from duodenum varies with meal volume, because volume distension of the stomach stimulates gastric peristalsis and gastric emptying. If, on the other hand, ingested nutrients are not diverted from the duodenum, the speed of gastric emptying (intestinal nutrient entry) of even high volume meals is limited (to ≤3 kcal/min in humans), because inhibitory feedback from downstream intestinal sensors increases with the rate of gastric emptying as the length of intestinal contact increases [12.]. Normally, except after very large meals, this balance between propulsive drive and inhibition limits nutrient exposure to proximal bowel.

When encapsulated in small, enterically coated pellets and ingested with food, small amounts of specifically stimulating nutrient digestive products can suffice to evoke a large response. Ingestion of such pellets with food spreads the pellets along the small intestine for hours, during which the specifically exciting nutrient is gradually released from the enteric coating. By "small" is meant pellets in the range of approximately 0.5 mm to approximately 3 mm in diameter. For example when pellets coated with a pH sensitive coating designed to release at ileal pH (7.2-7.4) enter the proximal ileum, release starts and continues as the pellets are transported over considerable, if not the entire, ileal length. While release from the first arriving pellets continues during ileal transit, each pellet newly arriving into the ileum begins anew this process of slow release. Thus, even though the first arriving pellets have already left the proximal ileum to continue their release more distally, newly arrived pellets begin to release in proximal ileum. Together, the newly and previously arrived pellets create a long swath of ileal release. Heterogeneities (coating thicknesses, pellet diameters) among pellets also serve to elongate the region of nutrient contact. These processes are repeated continuously as long as pellets continue to empty from the stomach and subsequently enter the ileum. The long swath of nutrient contact so established will evoke a high sensory response, so long as the concentration of nutrient at the local villus surface is higher than the threshold for peptide or serotonin release. Threshold concentrations of fatty acid sufficient to release GLP-1 or PYY from enriched cultures of L cells ranged from 0.1-0.15 mM in various reports, levels that are probably considerably lower than concentrations that can be released locally from pellets.

CTM #3 consists of pellets of approximately 1.4 mm diameter (median) of lauric acid (active ingredient) coated with Eudragit L100 to provide ileal delivery of the active ingredient. The pertinent details concerning other characteristics of CTM #3 will now be presented: first its transit characteristics; then the solubility of its active ingredient, lauric acid; its effects in patients with type 2 diabetes; and finally information on its dose-responses.

FIG. 1 shows a standard U.S.P. (United States Pharmacopeia) in vitro dissolution tests: (1 g of pellets; rotating basket (100 rpm); 900 ml of medium) that demonstrates cumulative dissolution of a water-soluble, pharmacokinetic marker N-acetyl-p-aminophenol (APAP) (AKA acetaminophen) and the active nutrient (maltose) in CTM #1 (FIG. 1a) and the active nutrient (lauric acid) in CTM #3 (FIG. 1b and FIG. 1c). In FIG. 1a, the Eudragit L30D55 enteric coating of CTM #1 prevented dissolution at simulated gastric pH (pH 2.5) but allowed rapid and full dissolution of both maltose and APAP over a one hour period at simulated jejunal pH (pH 6.2). Once the coating disintegrates at pHs>5.5, maltose is as rapidly and fully soluble as APAP and shows no pH dependence of solubility. Therefore, at what point maltose is released in the gut depends entirely on when/where the enteric coating disintegrates. In FIG. 1b uncoated cores of CTM #3 (lauric acid) were incubated at simulated jejunal pH (pH 6.2) for one hour, followed by simulated ileal pH (pH 7.2) for 3 hours. The graph illustrates that in the absence of any restrictive coating, in a bile-free medium, lauric acid is much less soluble than maltose and that its aqueous solubility is pH-dependent (it becomes more soluble as it ionizes at higher pHs such as pH 7.2). FIG. 1c illustrates how uncoated cores of CTM #3 dissolve in a medium that contains concentrations of bile salts and lecithin similar to those found in ileal fluid. Although the simulated bile increases luminal dispersion of the lauric acid due to uptake into bile-lecithin micelles, lauric acid is still only half as soluble as maltose at pH 6.2 but becomes as soluble as maltose or APAP at pH 7.2. Colonic pH may be as low as pH 5.5-6.0 in cecum (because of bacterial fermentations) but rises to pH 7.0 by the mid transverse colon and beyond. However, concentrations of bile salts and lecithin (which promote solubility of fatty acids) are markedly diminished in the colon. The fact that CTM #3 (as discussed further below) continued to lower blood glucose and to release GLP-1 and/or PYY from 240 min after ingestion onwards, when almost all pellets were in the colon, indicates that lauric acid released in the colon was sufficiently stable and sufficiently soluble to be bioactive despite the abundance of colonic bacteria and the paucity of bile salts.

Figure 2A:
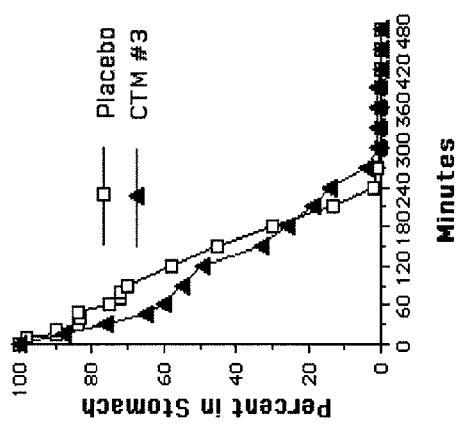

The graph of FIG. 2a depicts the average gastric emptying (in eight normal subjects) of 10 g of coated pellets of lauric acid ("CTM #3", 47% lauric acid w/w) with median diameters of 1.4 mm versus average gastric emptying (in five other normal subjects) of 10 g of inert (non-nutrient), placebo pellets with slightly larger median diameters. The pellets were coated in a manner to ensure content release in the ileum. Gastric emptying was determined by gamma scintigraphy of an additional 1 g of pellets (of either CTM #3 or placebo) surface-labeled with 99Tc-polymethyl methacrylate [13.]. added to the 10 g doses. In both groups of subjects, pellets were ingested with a 415 kcal breakfast following an overnight fast. Two features of this graph are pertinent. First, it is evident that lauric acid released in the ileum (as shown further below) did not inhibit the gastric emptying of the pellets; that is, the emptying rates of CTM #3 were the same as those of the inert, placebo pellets. Small bowel transit times for pellets of placebo and CTM #3 were, respectively, 121±4 min and 137±17 min, not statistically significantly different from each other and each significantly shorter than the literature average time of 203±20 min. Thus, there was no evidence that lauric acid activated the ileal brake. Second, both types of pellets began to empty promptly after ingestion and continued to empty in a steady fashion for nearly four hours. This immediate and steady pattern of gastric emptying ensures that a very wide swath of bowel (including the ileum and/or the colon) will be bathed continuously by lauric acid for >4 h, beginning between 12 and 31 minutes after ingestion of the pellets. Third, the regression line FIG. 2b depicts 15 data points (fewer are apparent, because several of the points were identical among subjects and thus overlap) of the gastric emptying of lauric acid pellets (CTM #3) when taken in doses of 5, 10, 15, or 20 grams by 13 normal volunteers. Gastric emptying of these pellets is expressed as kilocalories (kcal) per minute, a value calculated by multiplying the slopes of the emptying time courses (%/min/100) by grams of pellets ingested which is in turn multiplied by nine times the weight of lauric acid/gram of pellets (that is, 9 kcal per gram). The FIG. 2b graph illustrates that over this range of doses, the amount of nutrient ultimately bathing the distal gut per unit time depends on grams of pellets ingested. This means that fractional emptying of pellets is constant and that, the time for pellets to completely empty from the stomach is independent of dose (data not shown). Although the gastric emptying of food (specifically of carbohydrate) was not measured in these experiments, it is known from many observations that a meal of this size (415 kcal) will empty completely over about four hours. Thus, the pellets emptied concurrently with the carbohydrate meal.

Figure 3B:
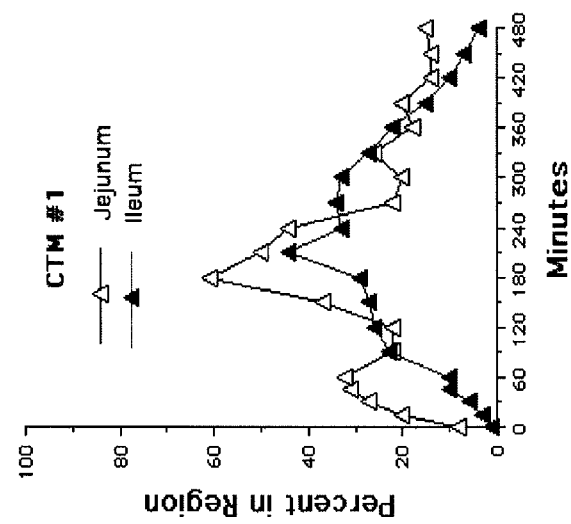
FIG. 3b shows the damming up of pellets in the jejunum.
Figure 3A:
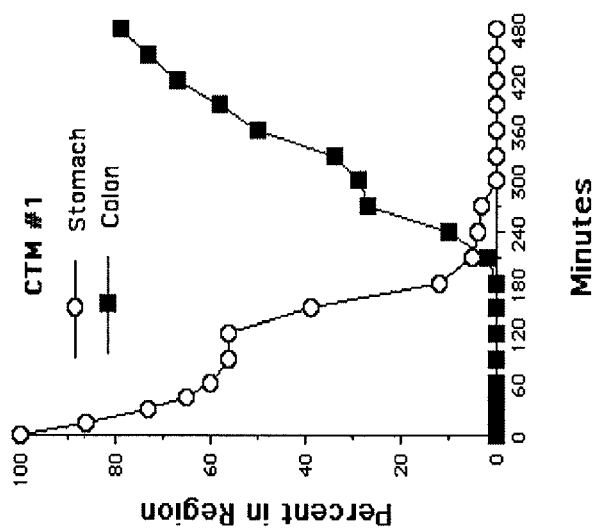
FIG. 3a the effect on gastric emptying.

By contrast, FIG. 3 illustrates what will happen when the CTM pellets inhibit gastrointestinal transit, so that movement of the pellets themselves is slowed and the pellets do not reach the ileum in great numbers until 90 minutes after ingestion. FIGS. 3a and 3b shows time-courses of regional distributions of pellets in five normal subjects who ingested CTM #1 which was formulated with a more rapidly releasing coating of Eudragit L30 D55 (dissolves above pH 5.5). CTM #1 contained 47% maltose (active ingredient), whereas CTM #3 was formulated with Eudragit L100 (which dissolves above pH 6.0) and contained 47% lauric acid as the active ingredient. (The remaining weight of the CTM pellets is the coating and excipients.) Evident in the FIG. 3a graph is a period of reduced gastric emptying from 60-150 min. Notice that the colon did not begin to fill until after 210 min. The FIG. 3b graph illustrates a damming up of pellets in the jejunum, so that ileal occupancy by pellets was low until 90 min. Small bowel transit time was 219±20 min, 80 minutes longer than that of CTM #3. Analyses of individual time-courses demonstrated that 60% of APAP release occurred in the mid to distal jejunum and 40% in the proximal to mid ileum. Since CTM #3 did not evoke ileal braking, it is ideal for delivery of active ingredient to ileum in the early post cibal period.

Figure 4B:
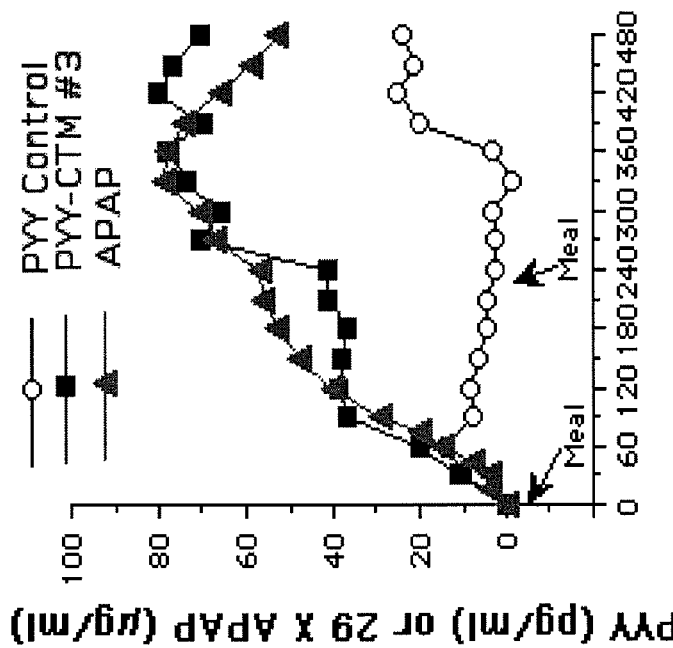
FIG. 4b depicts the PYY and APAP time-courses for four of these eight subjects.
Figure 4A:
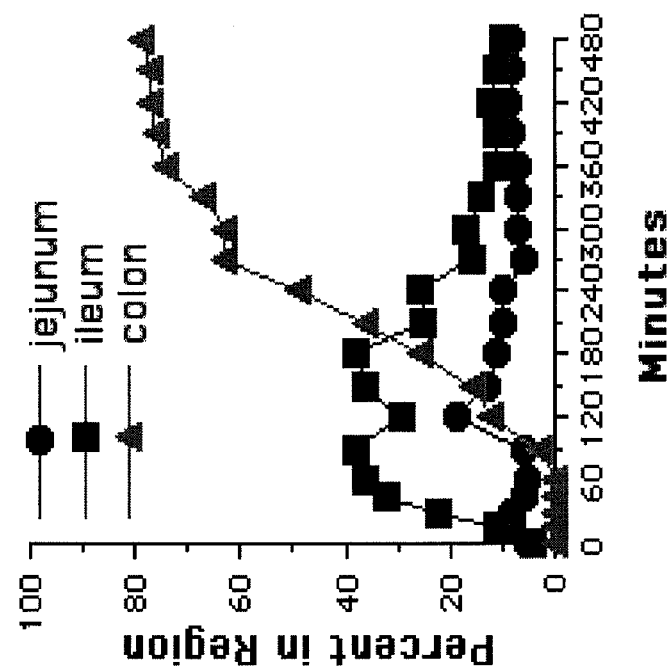
FIG. 4a shows the average time-courses For CTM #3 distribution from eight normal subjects.

FIG. 4a shows the time-courses of jejunal, ileal and colonic occupations by pellets in eight normal subjects who took 10 g of the CTM #3 pellets with a standard breakfast meal (415 kcal; 71 g carbohydrate) at t=0 min. An additional gram of pellets was added to the dose; and the additional pellets had been surface-labeled with 99m-Tc-polymethylmethacrylate (these additional pellets could not release their contents), so that the positions of the pellets with time could be followed with a gamma camera. The releasing pellets also contained 5% (w/w) APAP which is rapidly and completely absorbed from small or large bowel, even in the presence of food. The APAP served as a pharmacokinetic marker. Subjects ate a free-choice meal at 241 min. Finally, PYY levels (see FIG. 4b) were followed on CTM and also on control days when four of the eight subjects shown in FIG. 4a consumed the standard breakfast at t=0 and a free choice lunch at t=241 min, but no pellets of CTM #3. Because lauric acid released from CTM #3 cannot be distinguished in plasma from dietary and endogenous lauric acid, assays of plasma PYY served as a surrogate for the release of bioactive lauric acid, which is known to be a potent stimulus of secretion of PYY and GLP-1 from L cells. To compare the time-courses of basal subtracted PYY measurements with those of APAP, analytical values for APAP were scaled up so that they equaled the peak PYY at 300 min.

In contrast to the pellets of CTM #1 (FIG. 2), FIG. 4a shows that the pellets of CTM #3 were so rapidly swept through jejunum that already by 60 minutes post cibal most pellets resided in ileum. From 240-300 minutes, the pellets began to empty from the ileum, so that by 300 min, there were few pellets in the small bowel, and the majority of pellets was now in the colon. FIG. 4b shows plasma concentrations of PYY (secreted by ileal and/or colonic L cells) and APAP. The figure shows that APAP began to be released within 12 minutes, when pellets were equally distributed between jejunum and ileum. From 60-240 min, APAP release came undoubtedly from pellets in the ileum, while after 300 min APAP release came almost entirely from pellets in the colon. Note that the general shape of the APAP and PYY curves were similar, indicating that although lauric acid is much less water soluble than APAP, it nevertheless was released in parallel with APAP. By comparing the time-course of APAP over the 480 min of observation with the time-courses of regional distributions of pellets in each individual of the eight subjects (instead of with the average values as depicted above), it was estimated that about 50% of APAP was released along the ileum and 50% (predominantly after 240 min) in the colon.

When the same analysis was applied to another four normal subjects who ingested 5 g of CTM #3 with the standard breakfast, the distributions of pellets with time and the time-course of APAP were similar and not statistically different from those after the 10 g dose (data not shown) on a percentage basis (of course, on an absolute basis, only half as many pellets occupied each region at any given time).

Figure 5:
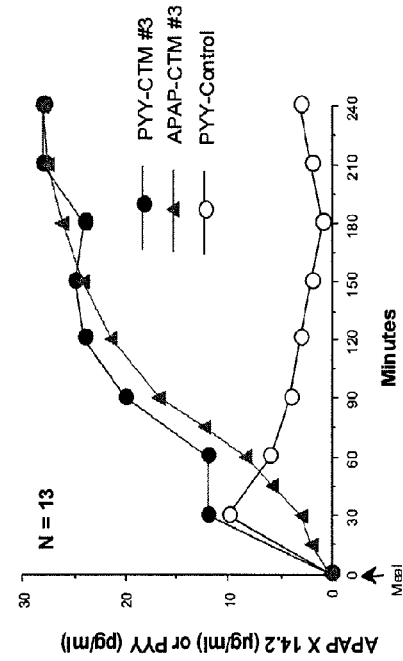
FIG. 5 shows an AUC analysis that demonstrates that CTM #3 can significantly increase PYY values.

FIG. 5 shows results from a larger group of 13 normal subjects who ingested 10 g of lauric acid containing CTM #3 versus 10 g of placebo pellets (in nine subjects) or no pellets (in four subjects) with the standard breakfast. At 30 min, PYY values following breakfast+CTM #3 were not significantly different from control values; but by 60 min PYY values for CTM #3 consumption were significantly higher than at 60 min in the control studies and remained much higher than corresponding control values over the period 60-240 min. From 60-240 min PYY rose in parallel with APAP. The measurements were not continued beyond 240 min because at that time the subjects consumed free choice (dissimilar) lunches.

The areas under the time-course curve (AUCs) for PYY following CTM #3 ingestion were six times higher than the AUCs for PYY following ingestion of the control meal ($p<0.0001$). Observations indicated that only an average of 28% of APAP was released by 240 min, though there was substantial variation among subjects. If one assumes that the amount of lauric acid released was also 28%, then the amount of lauric acid released was 0.28×4.7 g=1.32 g times 9 kcal/g=11.8 kcal of lauric acid. Thus, the approximately 12 kcal of lauric acid released from CTM #3 resulted in an AUC-240 for PYY that was 600% of the AUC-240 following the standard, 415 kcal breakfast without lauric acid pellets, of which 85% (353 kcal) had emptied by 240 min. On a per calorie basis, CTM #3 boosted PYY by 500%, so that it released 5×353/11.8=150 times as much PYY per calorie of lauric acid as did calories in this meal. The greater efficacy of CTM #3 over the breakfast alone arose in part from the fact that lauric acid was released in both the distal ileum and colon, where the concentrations of the PYY-bearing L cells are the highest; whereas PYY-releasing nutrients in the breakfast were likely digested and completely absorbed more proximally. Nevertheless, the very high per calorie difference undoubtedly also confirms that a release of lauric acid from the dosage form spread over a long swath of ileum and colon significantly magnified the response.

Figure 6B:
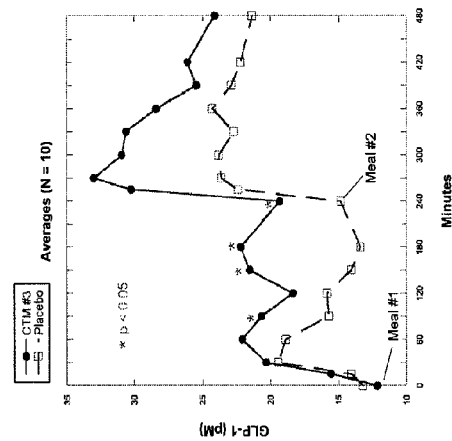
FIG. 6b shows the effect on post cibal plasma GLP-1
Figure 6A:
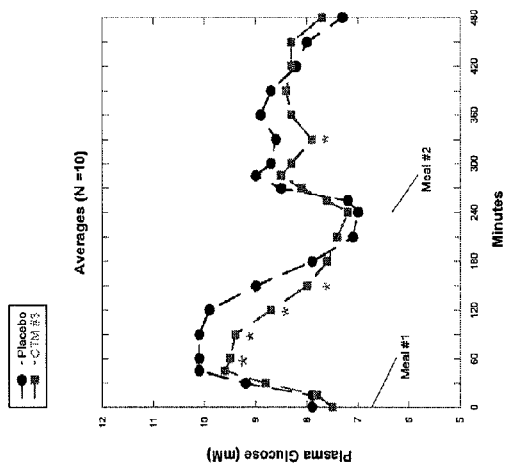
FIG. 6a shows the effect of CTM #3 on post cibal blood glucose.
Figure 7B:
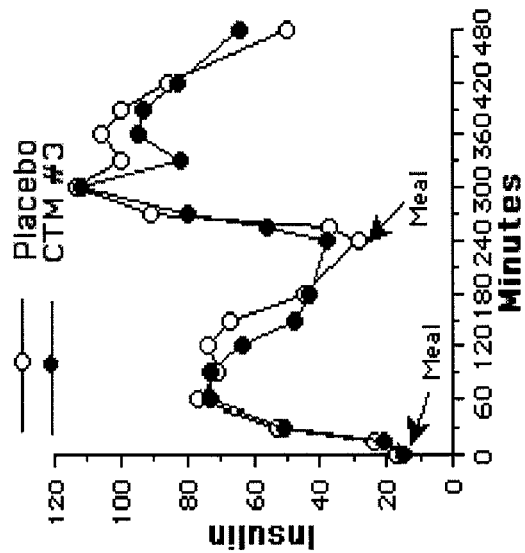
FIG. 7a shows the effect of CTM #3 on post cibal GIP, and FIG. 7b show the effect on post cibal plasma insulin.
Figure 7A:
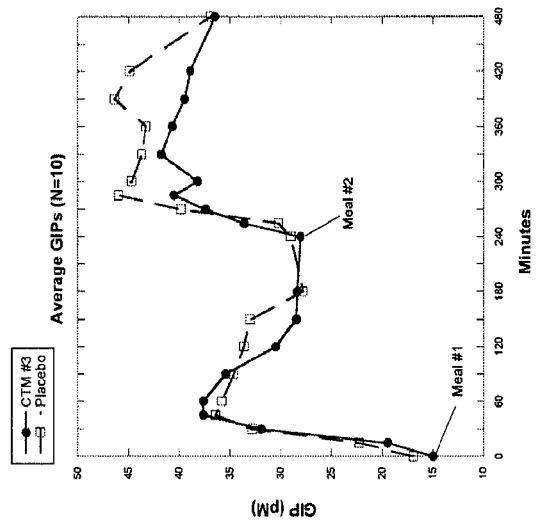

FIGS. 6 and 7 depict the effect of CTM #3 versus placebo on blood glucose in a randomized, placebo-controlled, double-blinded study in 10 subjects with mild to moderate type 2 diabetes. After an overnight fast, subjects ingested 10 g of placebo pellets or CTM #3 pellets with the same standard breakfast as above (415 kcal; 71 g of carbohydrate) followed by a standard lunch at 240 min (708 kcal; 89 g of carbohydrate). Plasma values, evaluated by repeated measures ANOVAs (analysis of variance), with time and treatment as factors, showed that the CTM vs. placebo: (A) (see FIG. 6a) lowered post cibal glucose after both meals, $p<0.05$, (with statistically significant treatment effects at 45, 60, 90, 120, 150, and 330 min); (B) (see FIG. 6b) elevated GLP-1, with statistically significant treatment effects at 90, 150, 180, and 240 min, evoking higher GLP-1s after lunch ($p<0.05$) but without time-treatment interactions; and (C) did not raise gastrointestinal insulin-releasing peptide (GIP) (see FIG. 7a) or plasma insulin (see FIG. 7b). Glucose lowering by the CTM #3 was more profound in subjects whose post cibal blood sugars rose above 9 mM while was of little effect in those with lower sugar levels; furthermore, the CTM treatment lowered glucose without raising insulin levels, effects consistent with known physiological actions of GLP-1. The higher calorie lunch raised GLP-1s more than the breakfast on placebo days; and the CTM raised the post lunch GLP-1s even more. That the CTM raised GLP-1s but not levels of GIP, which is distributed along duodenum and proximal bowel, indicated that CTM #3 released lauric acid in the ileum as opposed to the proximal bowel. The AUC 0-240 for GLP-1 was 3.44 times larger than the corresponding AUC for the placebo pellets. Using a similar calculation as used above for PYY, the per-calorie effectiveness of the lauric acid in CTM #3 in boosting the GLP-1 response to the meal was 77 times that of the calories in the breakfast.

Figure 8B:
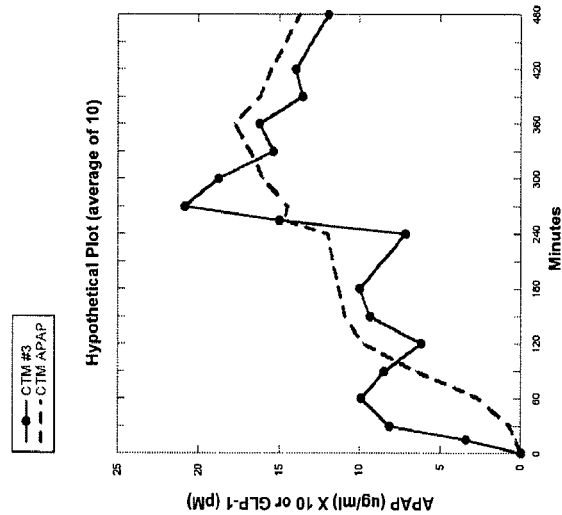
Figure 8A:
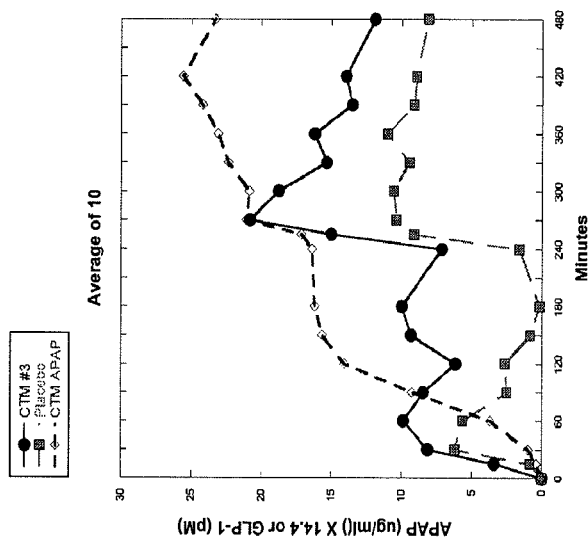
FIG. 8a shows the time courses of plasma APA and GLP-1 levels in diabetics following CTM #3 ingestion.

FIG. 8a shows time-courses of plasma APAP levels and basal-subtracted GLP-1 levels following CTM #3 treatment in the 10 diabetic subjects who ingested 10 g of CTM #3 with breakfast. For comparisons, the APAP levels have been scaled up so that their value equaled that of the GLP-1 peak at 270 min. Time to first detectable rise of plasma APAP levels in these diabetic subjects (31±7 min) was significantly (p<0.02, unpaired t test) longer than in 21 normal subjects (13±2 min) who ingested 10 g of CTM #3 with the same standard breakfast (see FIG. 5). The diabetic subjects were older than the normal subjects, and four of them had mild vagal neuropathy which might have contributed to slower gastric emptying. Moreover, hyperglycemia may slow gastric emptying, especially emptying of solids. Correspondences between the APAP and GLP-1 time-courses of CTM #3 were not as good as those between APAP and PYY time-courses after CTM #3 in normal subjects (see FIG. 5). If it is assumed that the high GLP-1 values evoked by the lunch (+placebo), which was higher in calories, fat, and protein, added to GLP-1 released by the CTM treatment after 240 min, then the peak GLP-1 at 270 min released by CTM #3 might have been around 12 pM without the contribution of the meal. In that case, if the line representing the CTM's APAP level had been scaled up to a 12 pM GLP-1 peak, APAP and GLP-1 time-courses for APAP and GLP-1 would be more similar. FIG. 8b illustrates this hypothesis and suggests a close temporal correspondence between APAP level and GLP-1 level. Thus, it is unlikely that there was a significant problem with the dissolution of lauric acid in these diabetics.

Figure 9B:
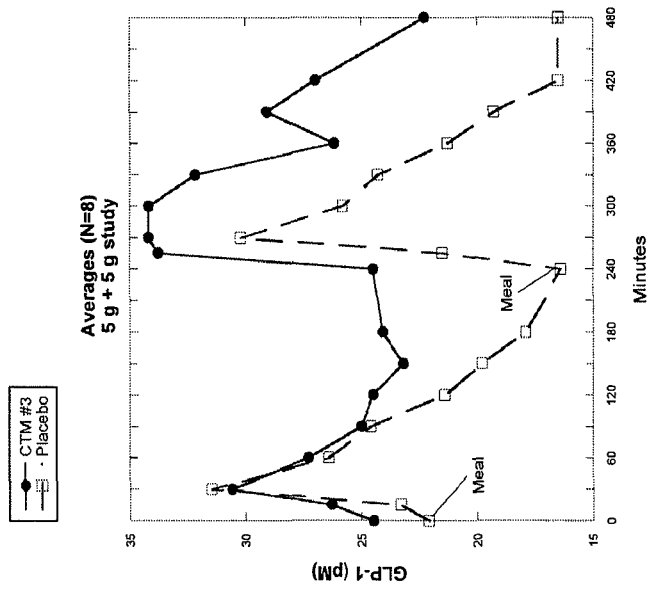
FIG. 9b illustrates the GLP-1 levels from the same experiment.
Figure 9A:
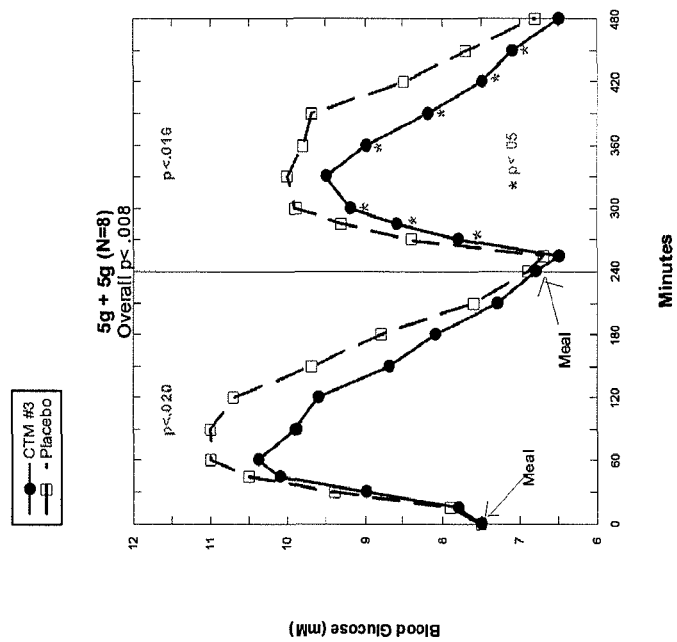
FIG. 9a illustrates the blood glucose levels from an experiment where two 5 g doses of CTM #3 are ingested each with a meal.

Because there appeared to be a continued effect of the morning 10 g dose in the preceding example with (a) high GLP-1 from 240 through at least 390 minutes and (b) significant depression of plasma glucoses at 330 minutes, this and the next trial was redesigned to assess whether there was a carry-over of the morning CTM #3 dose into the post lunch hours. Instead of using two different meals (with a high calorie, high fat and high protein lunch), the same breakfast meal was given at t=0 and again at t=241 minutes. FIG. 9a represents the blood glucose levels from an experimental limb in which 5 g of CTM #3 (vs. placebo) was given with breakfast and another 5 g was given with lunch in a double blinded trial. FIG. 9b shows the GLP-1 values from the same experiment. In the 5 g+5 g study in eight subjects, only one of the eight had peak post cibal control glucose below 8 mM, and this subject did not respond to CTM #3; that is, the subject's blood sugars were not lowered by the CTM treatment. However, the other seven subjects did respond. Because a glucose level of below 8 mM is essentially in the normal range, it appears that CTM #3 treatment lowers only abnormal blood glucose levels. Repeated analysis using ANOVA for time and treatment as factors, revealed a significant lowering of plasma glucose (p<0.02) by CTM #3, without a time-treatment interaction in the 0-240, post breakfast period. In the post lunch period (241-480 min), there was also a statistically significant lowering of plasma glucose, with treatment effects indicated by '*' in FIG. 9a. The effect of CTM #3 (vs. placebo) on GLP-1 in FIG. 9b was of borderline significance (p<0.07) in the 0-240 min period, but was highly significant (p<0.009) in the 241-480 min period, without a time-treatment interaction (repeated measurement ANOVA). The borderline effect in the 0-240 min period appears due to slow, initial release. Although the AUC 0-240 did not significantly differ from AUC 240-480 for GLP-1 after the meal+placebo, the afternoon AUC for GLP-1 was significantly higher than the morning AUC after meal+CTM #3. This finding confirms a carry-over effect of the morning CTM #3 dose that added to the effect of the lunchtime dose. After 240-300 minutes in normal subjects, scintigraphic studies have shown that almost all breakfast pellets were in the colon and continued to release APAP and PYY through 330 min. If it is assumed that there were similar transit times for pellets in these diabetic subjects, the above results indicate that CTM #3 is still capable of releasing GLP-1 from the largest concentrations of L cells in colon of diabetic patients, just as it had released PYY from colonic L cells of normal subjects.

Figure 10B:
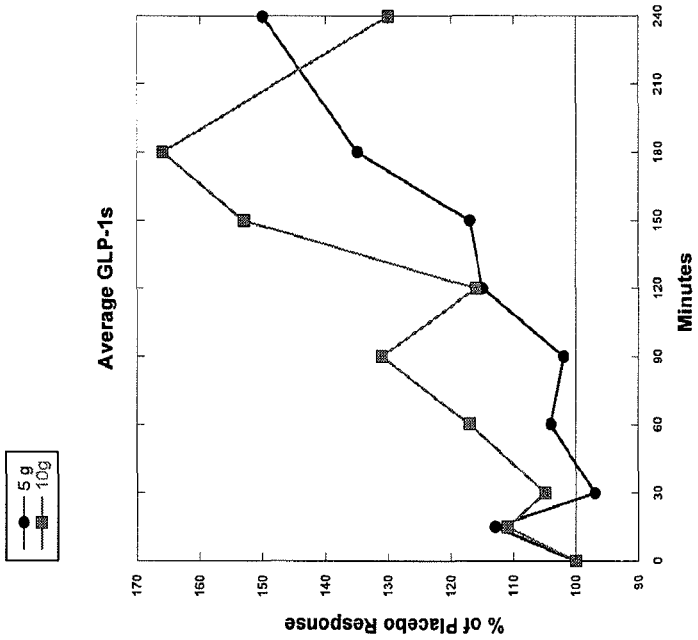
FIG. 10b shows GLP-1 levels over time following ingestion of either 5 g or 10 g of CTM #3 with a breakfast.
Figure 10A:
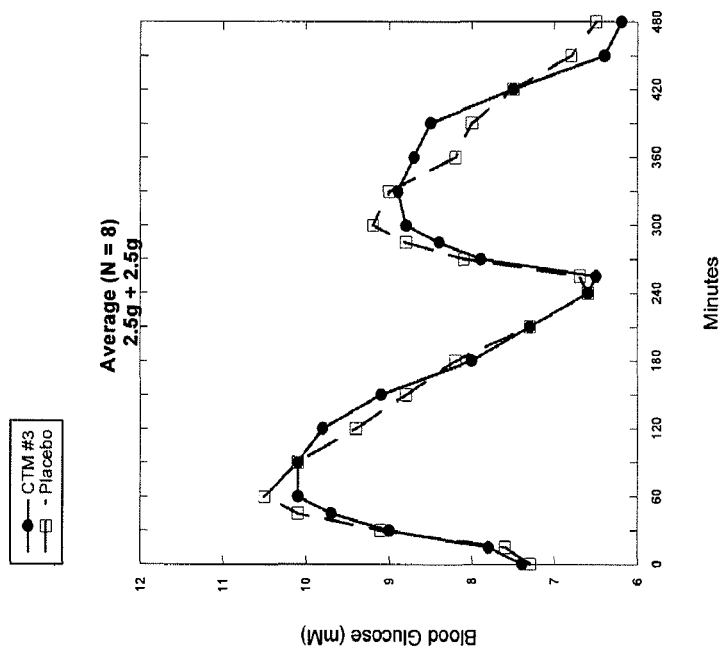
FIG. 10a shows the blood glucose level from an experiment similar to that of FIG. 9 except that two 2.5 g doses of CTM #3 were used.

When the study was repeated in mostly the same subjects (with all eight subjects having peak blood sugars >8.5 mM) with treatments of 2.5 g of CTM #3 (vs. placebo) with the standard breakfast and 2.5 g (vs. placebo) with the standard lunch, there was no longer a significant difference (CTM vs. placebo) in post cibal blood glucoses (FIG. 10a). FIG. 10b shows GLP-1 concentrations in blood at each sampling time over 0 to 240 minutes after 5 grams or 10 grams of CTM #3 were consumed with the standard breakfast. The GLP-1 values (vertical axis) following the CTM treatment are expressed as a percent of the corresponding value at each time point following the placebo treatment, so that any value above the horizontal 100% line represents the effect of lauric acid released from the CTM #3. At both dose levels, the positive slopes indicate an increasing effect of the CTM #3 with time, probably the result of an increasing amounts and spread of release along the ileum. The 10 g dose produced an earlier sustained rise above placebo value and a generally higher rise above placebo value throughout when compared to the 5 g dose. If an AUC from 0-240 min is calculated for a 100% value at each of the time points (to remove the area below the horizontal, 100% line) and this value is subtracted from the AUC 0-240 for the GLP-1 responses following the 10 g dose and likewise following the 5 g dose, the resulting delta AUCs for the 0-240 minute period can be calculated. Such a calculation indicates that the delta AUC-0-240 for the 5 g dose is about 33% of the delta AUC 0-240 of the 10 g dose, instead of 50% that might be expected. This analysis indicates that whatever the concentrations of lauric acid that reached L cells along the ileal length following the 5 g dose, these sensory cells were responding less than maximally.

According to the present disclosure one can add an enterically coated nutrient dosage of no more than 42 kcal to a meal and because the encapsulated nutrient is released over considerable time and length of the distal bowel effector molecules such as PYY and GLP-1 are increased several fold as compared to the meal alone. In the case of encapsulated lauric acid each kcal of lauric acid is more than 50 times (often more than 100 times or even 150 times) as effective (bioeffect) as a kcal of normally ingested food in releasing effector molecules such as PYY and GLP-1. As a result of the greatly increased bioeffectiveness of the nutrient dosage, the blood sugar level of type 2 diabetics ingesting the dosage is significantly lowered. Furthermore, the addition of 42 kcal or less is essentially insignificant to the overall food intake of the patients and is insufficient to promote weight gain. That type 2 diabetes can be modulated by a safe and easily ingested nutrient composition is an exciting and significant breakthrough.

The following claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described preferred embodiment can be configured without departing from the scope of the invention. The illustrated embodiment has been set forth only for the purposes of example and that should not be taken as limiting the invention. Therefore, it is to be understood that, within the scope of the appended claims, the invention may be practiced other than as specifically described herein.

REFERENCES

1. Dixon J B, O'Brien P E, Playfair J, Chapman L, Schachter L M, Skinner S, Proietto J, Bailey M, Anderson M. Adjustable gastric banding and conventional therapy for type 2 diabetes. J Am Med Assn, 2008. 299:316-323.
2. Pories W J et al. The Control of Diabetes Mellitus (NIDDM) in the Morbidly Obese with the Greenville Gastric Bypass. Annals of Surgery, 1987. 316-23.
3. Ropert A, et al. Colonic fermentation and proximal gastric tone in humans. Gastroent, 1996. 111:289-296.
4. Feltrin K J et al. Effects of intraduodenal fatty acids on appetite, antropyloroduodenal motility, and plasma CCK and GLP-1 in humans vary with chain length. Am J Phsyiol, 2004. 287: R524-33.
5. Enc F Y et al. Inhibition of gastric emptying by acarbose is correlated with GLP-1 response and accompanied by CCK release. Am J Physiol, 2001. 281: G752-G763.
6. Hucking K et al. Diabetic Medicine, 2005. 22:470-476.
7. Vilsboll T, et al. Incretin secretion in relation to meal size and body weight in healthy subjects and people with type 1 and type 2 diabetes. J Clin Endocrinol Metab, 2003. 88:2706-2713.
8. Toft-Nielsen M, et al. Determinants of impaired secretion of glucagon-like peptide-1 in type 2 diabetic patients. J Clin Endocrin Metab, 2001. 86:3717-23.
9. Ma J, et al. Effects of a protein preload on gastric emptying, glycemia, and gut hormones after a carbohydrate meal in diet-controlled Type 2 diabetes. Diabetes Care, 2009. 32:1600-1602.
10. Nilson M et al. Metabolic effects of amino acid mixtures and whey protein in healthy subjects: studies using glucose equivalent drinks. Am J Clin Nutr, 2007. 85:996-1004.
11. Zhao X T et al. J Nutr, 1997. 127:2350-2356.
12. Lin HC et al. Inhibition of gastric emptying by glucose depends on the length of the intestine exposed to the nutrient. Am J Physiol, 1989. 256: G404-G411.
13. Meyer J H, Lake R, Elashoff J D. Post cibal gastric emptying of pancreatin pellets: Effects of dose and meal oil. Dig Dis Sci, 2001. 46:1846-1852.

What is claimed is:

1. A method for directly lowering blood sugar levels in subjects having type 2-diabetes comprising the steps of:
    (i) providing pellets comprising lauric acid as an active ingredient enterically coated with poly(methacrylic acid-co-methyl methacrylate), releasing the active ingredient at a pH higher than pH 6.0 so that the pellets their contents over an extended length of the ileum and/or colon of the intestine of the subject; and
    (ii) administering a dose of the pellets together with a meal to a subject having type-2 diabetes so that the pellets enter the intestine of the subject along with the meal and release their contents over an extended period of time extending the length of the intestine contacted by the released contents so that effector molecules are released and blood sugar levels in said subject are decreased for an extended period of at least two hours.

2. The method according to claim 1, wherein the coated pellets have a mean diameter between about 0.5 and about 3.0 mm.

3. The method according to claim 2, wherein the coated pellets have a mean diameter of about 1.4 mm.

4. The method according to claim 1, wherein the extended period of time is at least 240 minutes.

5. The method according to claim 1, wherein the enteric coating dissolves at a pH higher than pH 5.5.

6. The method according to claim 1, wherein the enteric coating is designed to release the nutrient in the colon.

7. The method according to claim 1, wherein the step of administering is repeated at least one time so that doses of pellets are administered with at least two successive meals.

8. The method according to claim 1, wherein the dose of pellets has a kilocalorie value of less than 50 kilocalories.

9. The method according to claim 8, wherein the dose of pellets has a kilocalorie value of less than 25 kilocalories.

10. The method according to claim 1, wherein the dose of pellets is at least 50 times more effective at eliciting effector molecules on a kilocalorie basis than the meal.

11. The method according to claim 1, wherein the dose of pellets is at least 100 times more effective at eliciting effector molecules on a kilocalorie basis than the meal.

* * * * *